United States Patent
Machida

(10) Patent No.: US 7,695,428 B2
(45) Date of Patent: Apr. 13, 2010

(54) ENDOSCOPE APPARATUS

(75) Inventor: Mitsunori Machida, Saitama (JP)

(73) Assignee: Fujifilm Corporation, Tokyo (JP)

( * ) Notice: Subject to any disclaimer, the term of this patent is extended or adjusted under 35 U.S.C. 154(b) by 763 days.

(21) Appl. No.: 11/092,556

(22) Filed: Mar. 29, 2005

(65) Prior Publication Data

US 2005/0215855 A1 Sep. 29, 2005

(30) Foreign Application Priority Data

Mar. 29, 2004 (JP) ............................. 2004-096453
Nov. 5, 2004 (JP) ............................. 2004-322793

(51) Int. Cl.
*A61B 1/00* (2006.01)

(52) U.S. Cl. .................. 600/114; 600/115; 600/118; 600/156

(58) Field of Classification Search ......... 600/114–118, 600/128–130, 156, 20; 128/898; 604/172
See application file for complete search history.

(56) References Cited

U.S. PATENT DOCUMENTS

| 4,681,093 | A | * | 7/1987 | Ono et al. ................... 600/116 |
| 6,077,219 | A | * | 6/2000 | Viebach et al. ............... 600/114 |
| 6,554,793 | B1 | | 4/2003 | Pauker et al. |
| 6,840,900 | B2 | * | 1/2005 | Smith ......................... 600/104 |
| 2002/0058859 | A1 | * | 5/2002 | Brommersma ............... 600/156 |
| 2002/0072651 | A1 | * | 6/2002 | Vilos ........................... 600/105 |
| 2003/0187428 | A1 | * | 10/2003 | Lane et al. ..................... 606/21 |
| 2003/0220544 | A1 | * | 11/2003 | Chang ......................... 600/156 |
| 2003/0229269 | A1 | | 12/2003 | Humphrey |
| 2004/0038534 | A1 | * | 2/2004 | Taylor ......................... 438/690 |
| 2005/0215989 | A1 | * | 9/2005 | Abboud et al. ................ 606/21 |
| 2006/0106321 | A1 | * | 5/2006 | Lewinsky et al. ........... 600/491 |

FOREIGN PATENT DOCUMENTS

| JP | 10-248794 | 9/1998 |
| JP | 2001-340462 | 12/2001 |
| JP | 2002-301019 | 10/2002 |

* cited by examiner

*Primary Examiner*—John P Leubecker
*Assistant Examiner*—Victoria W Chen
(74) *Attorney, Agent, or Firm*—Young & Thompson

(57) ABSTRACT

In an endoscope apparatus of the present invention, an one-side gap between a tube main body of an overtube and an insertion portion is set at 0.5 mm to 1.5 mm. Lubricity is improved because a lubricating liquid such as water supplied from the injection port to the base end side of the tube main body is sufficiently supplied to the whole area of the gap between the tube main body and the insertion portion by setting the one-side gap at not less than 0.5 mm. Also, the snaking of the insertion portion with respect to the tube main body can be held to a minimum by setting the one-side gap at not more than 1.5 mm. As a result of this, the insertion and extraction operability of the insertion portion with respect to the overtube is improved.

2 Claims, 6 Drawing Sheets

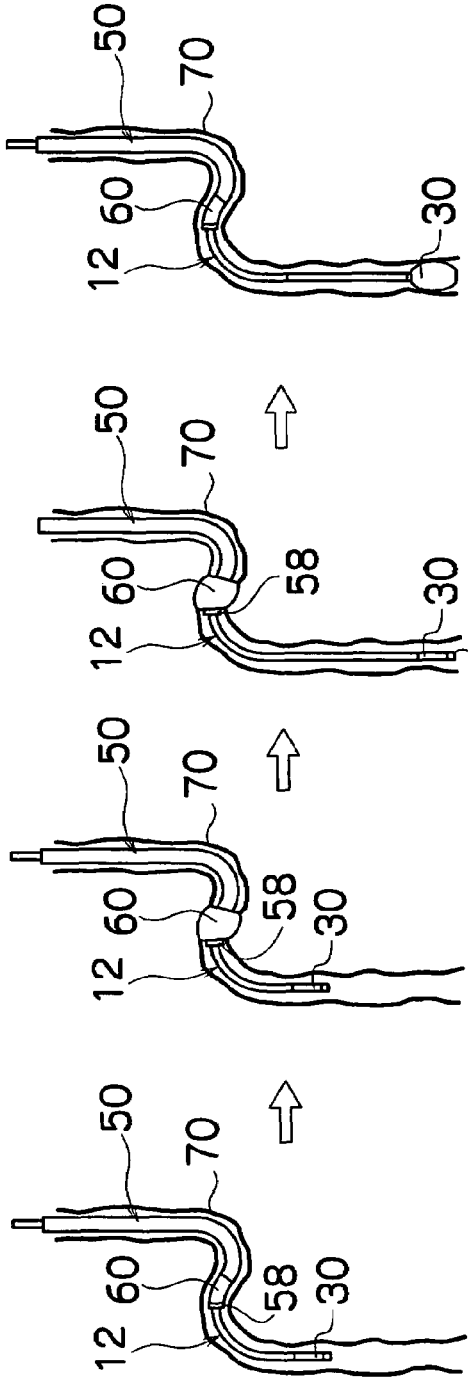

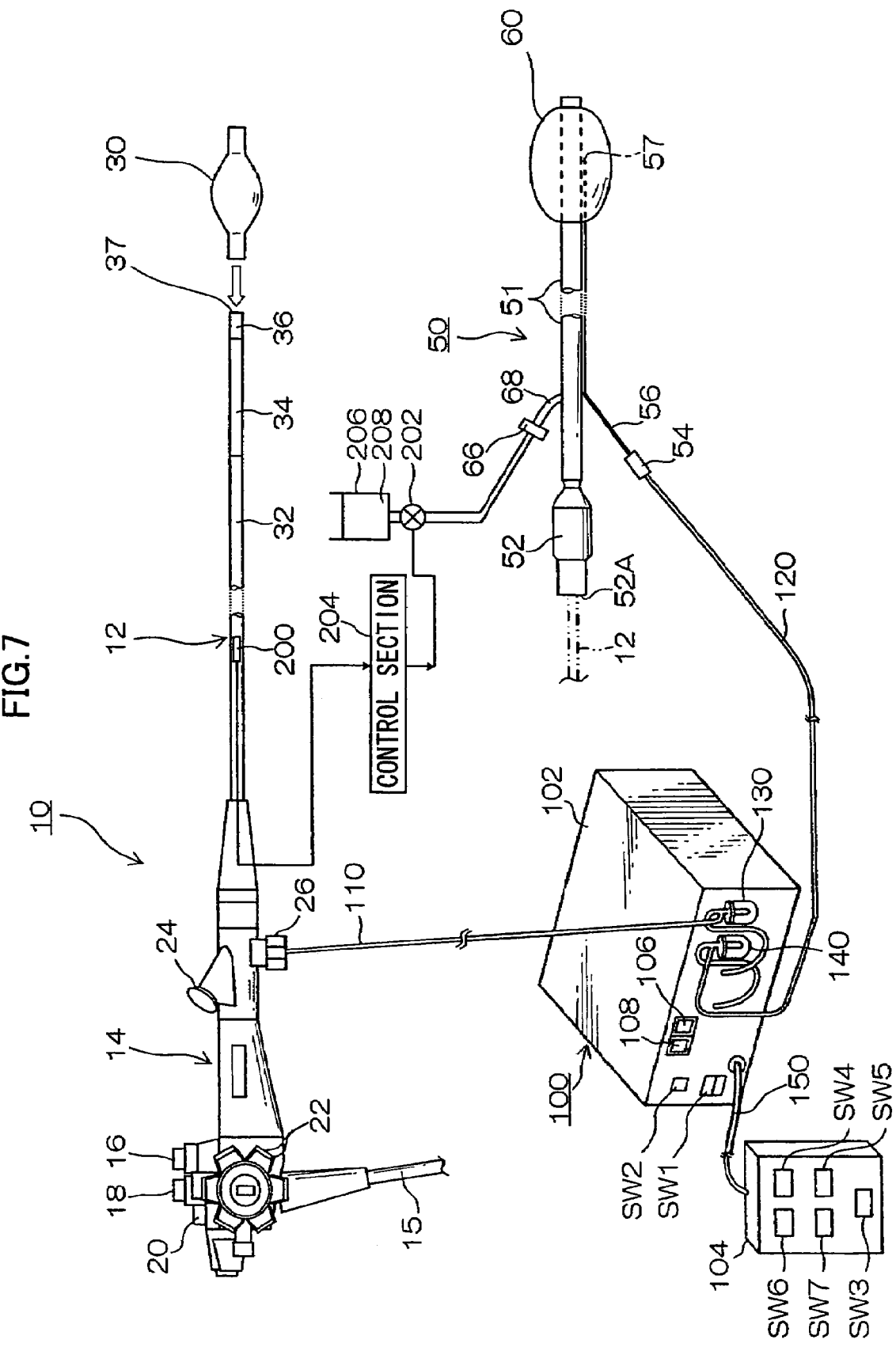

ENDOSCOPE APPARATUS

BACKGROUND OF THE INVENTION

1. Field of the Invention

The present invention relates to an endoscope apparatus and, more particularly, to an endoscope apparatus that has an endoscope in which a balloon is attached to a leading end of an insertion portion, and an insertion aid which guides the insertion portion of this endoscope into a body cavity.

2. Related Art

When the insertion portion of an endoscope is to be inserted into deep digestive organs such as the small intestine, force is not easily transmitted to the leading end of the insertion portion due to the complicated curvatures of the intestinal tract only by pushing in the insertion portion and hence insertion into deep parts is difficult. Therefore, there have been proposed endoscope apparatus that prevent extra curvatures and deflections of the insertion portion by inserting into a body cavity the insertion portion of an endoscope to which an insertion aid called an overtube or a sliding tube is attached and by guiding the insertion portion by use of this insertion aid (for example, Japanese Patent Application Laid-open No. 10-248794).

Also, there have been known conventional endoscope apparatus of the double-balloon type in which a first balloon is provided in the leading end portion of the insertion portion of an endoscope and a second balloon is provided in the leading end portion of an insertion aid (for example, Japanese Patent Application Laid-open No. 2001-340462 and Japanese Patent Application Laid-open No. 2002-301019).

In an endoscope apparatus of the double-balloon type, there is a case where the operation is such that the insertion portion and the insertion aid are inserted into the intestinal tract along a predetermined length and, with the first balloon and the second balloon inflated and kept fixed to the intestinal wall, the insertion portion and the insertion aid are simultaneously pulled toward the surgical operator, whereby the intestinal tract having been curved is caused to contract straight. After that, by repeatedly performing the insertion operation of the insertion portion, the insertion operation of the insertion aid and the above-described operation of pulling toward the surgical operator in this order, whereby the intestinal tract is pulled nearer and the insertion portion is inserted into an aimed part.

SUMMARY OF THE INVENTION

However, in none of the above-described conventional endoscope apparatus, an optimum value is set for the gap between the insertion aid and the insertion portion of an endoscope. The insertion aid is provided with a supply tube that supplies a lubricating liquid such as water to the above-described gap in order to improve the lubricity of the insertion portion of an endoscope. When the above-described gap is too small, the lubricating liquid is not sufficiently supplied. Conversely, when the gap is increased too much, the insertion portion of an endoscope snakes with respect to the insertion aid. Thus, the conventional endoscope apparatus had the problem that it is impossible to perform smooth insertion and extraction operations of the insertion portion of an endoscope with respect to the insertion aid.

The present invention has been made in view of such circumstances and has as its object the provision of an endoscope apparatus that improves the lubricity by a lubricating liquid and the insertion and extraction operability of the insertion portion of an endoscope by setting the gap between the insertion aid and the insertion portion of an endoscope at an optimum value.

In the first aspect of the present invention, to achieve the above object, there is provided an endoscope apparatus, comprising: an endoscope; an insertion aid into which an insertion portion of the endoscope is inserted; and a lubricating liquid supply device that supplies a lubricating liquid to a gap between the insertion aid and the insertion portion of the endoscope. In this endoscope apparatus, an one-side gap between the insertion aid and the insertion portion of the endoscope is set at 0.5 mm to 1.5 mm.

According to the first aspect, because an one-side gap between the insertion aid and the insertion portion of the endoscope is set at not less than 0.5 mm, a lubricating liquid such as water is sufficiently supplied to the gap and hence lubricity can be improved. Also, because the one-side gap is set at not more than 1.5 mm, the snaking of the insertion portion of the endoscope with respect to the insertion aid can be held to a minimum and hence the insertion and extraction operability of the insertion portion of the endoscope can be improved.

The feature of the second aspect of the present invention is that in the first aspect, a balloon capable of inflating and deflating is attached to an outer peripheral part of a leading end of the insertion portion of the endoscope and/or an outer peripheral part of a leading end of the insertion aid.

In the second aspect, the present invention relates to an endoscope apparatus which comprises an endoscope in which a balloon is attached to an outer peripheral part of a leading end of the insertion portion and an insertion aid which guides the insertion portion of this endoscope and to which a balloon is attached.

Because in such an endoscope apparatus, an one-side gap between the insertion aid and the insertion portion of the endoscope is are at not less than 0.5 mm, a lubricating liquid such as water is sufficiently supplied to this gap and hence lubricity is improved. Also, because the one-side gap is set at not more than 1.5 mm, the snaking of the insertion portion of the endoscope with respect to the insertion aid can be held to a minimum and hence the insertion and extraction operability of the insertion portion of the endoscope can be improved.

Incidentally, in a treatment with the aid of an endoscope apparatus in which an insertion aid is used, there is a case where after the insertion of the insertion aid and the insertion portion of the endoscope into an aimed part within a body cavity, operative instruments, such as a balloon dilator that dilates the narrow areas of the intestinal tract and a contrast medium tube that injects a contrast medium for observing narrow areas of the intestinal tract are inserted to perform a desired treatment. In this case, it is conceivable that only the insertion portion of the endoscope is extracted, with the insertion aid kept remaining in the body cavity, and that these operative instruments are inserted by using the insertion aid as a guide. Accordingly, it becomes necessary that in an endoscope apparatus of the balloon type, a balloon which has been deflated be removed via a gap between the insertion aid and the insertion portion of the endoscope. However, the thickness of a balloon made of natural rubber is as small as about 0.1 mm and the thickness of creases formed by the deflation of the balloon is also about 0.3 mm. Therefore, because in an endoscope apparatus of the present invention in which the one-side gap is set at not less than 0.5 mm, the balloon can be extracted without resistance, the insertion portion of the endoscope can be extracted from the insertion aid without problems.

The feature of the third aspect of the present invention is that in the first or second aspect, a sensor that measures a load resistance value between the insertion portion of the endoscope and the insertion aid is provided and the lubricating liquid supply device supplies a lubricating liquid on the basis of a load resistance value measured by the sensor.

Because this lubricating liquid is used to lessen load resistance between the insertion portion of the endoscope and the insertion aid, it is unnecessary to constantly supply the lubricating liquid from the lubricating liquid supply device. For this reason, load resistance between the insertion portion of the endoscope and the insertion aid is measured with the sensor and the lubricating liquid supply device performs the supply of the lubricating liquid when a measured load resistance value exceeds a prescribed value. As a result of this, the lubricating liquid can be saved because useless supply of the lubricating liquid can be prevented. Also, because relative insertion and extraction resistance of the insertion portion of the endoscope and the insertion aid becomes almost constant, stable operative treatment becomes possible.

According to an endoscope apparatus related to the present invention, the one-side gap between the insertion aid and the insertion portion of the endoscope is set at not less than 0.5 mm and, therefore, a lubricating liquid such as water is sufficiently supplied to the above-described gap, resulting in improved lubricity. Also, because the one-side gap is set at not more than 1.5 mm, the snaking of the insertion portion of the endoscope with respect to the insertion aid can be held to a minimum and hence the insertion and extraction operability of the insertion portion of the endoscope can be improved.

BRIEF DESCRIPTION OF THE DRAWINGS

FIGS. 6A to 6H are each an explanatory drawing that shows how to manipulate an endoscope apparatus related to the present invention; and FIG. 7 is a system configuration diagram of an endoscope apparatus in which the supply of a lubricating liquid is automated.

DETAILED DESCRIPTION OF THE PREFERRED EMBODIMENT

A preferred embodiment of an endoscope apparatus related to the present invention will be described on the basis of the accompanying drawings.

Figure 1:
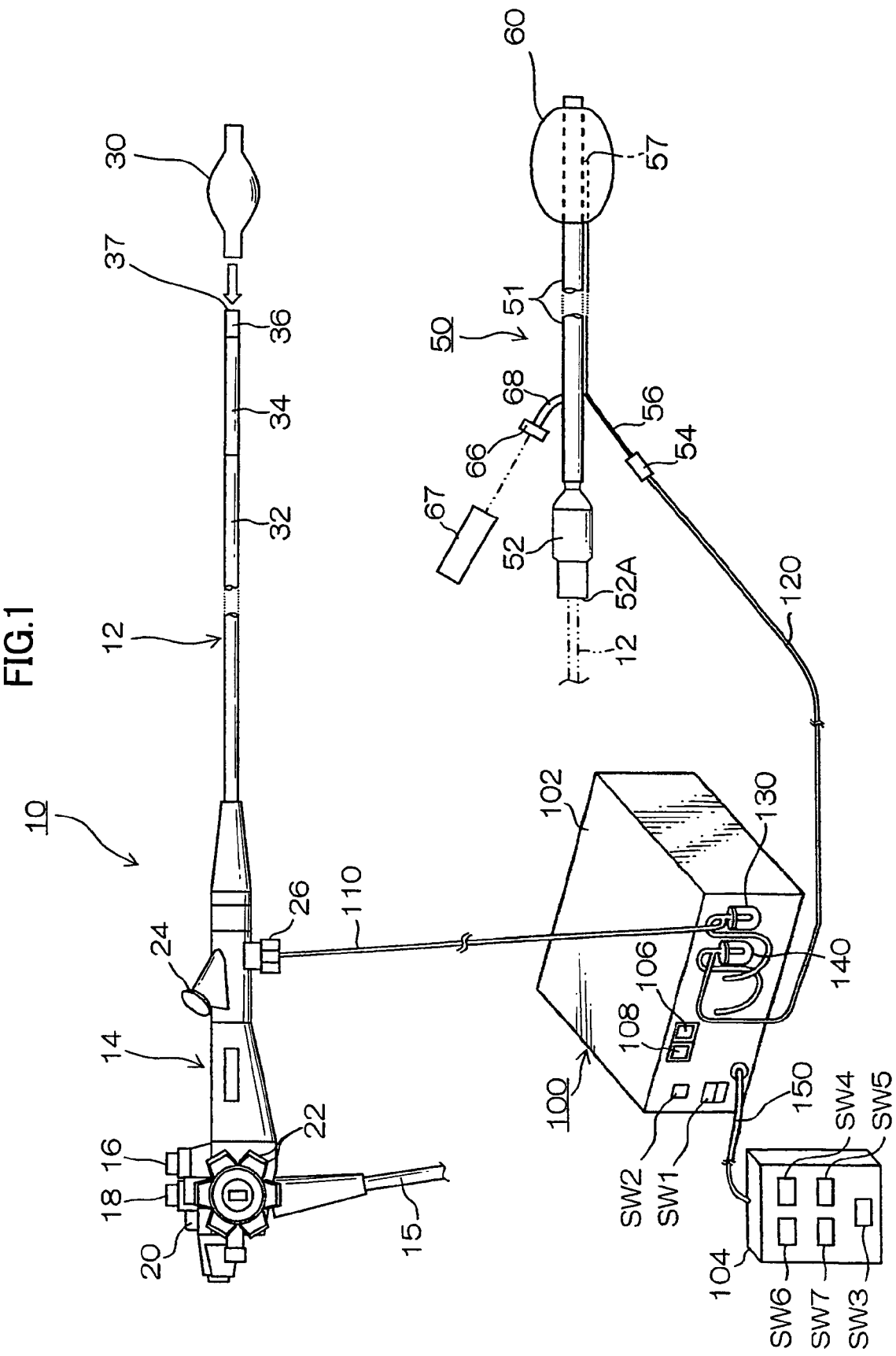
FIG. 1 is a system configuration diagram of an endoscope apparatus related to the present invention.

FIG. 1 shows a system configuration diagram of an endoscope apparatus related to the present invention. The endoscope apparatus shown in the figure is constituted by an endoscope 10, an overtube (an insertion aid) 50 and a balloon controller 100.

The endoscope 10 has a manipulation portion 14 and an insertion portion 12 that is provided in the manipulation portion 14 in a connected column arrangement. A universal cable 15 is connected to the manipulation portion 14, and a connector (not shown) to which a processor and a light source device (not shown) are connected is provided to the leading end of the universal cable 15.

In the manipulation portion 14 there are juxtaposed an air feed and water feed button 16, a suction button 18 and a shutter button 20 that are operated by the surgical operator and a pair of angle knobs 22 and a forceps insertion portion 24 are provided in their respective positions. Furthermore, the manipulation portion 14 is provided with a balloon air feed port 26 used to feed air to a first balloon 30 and suck air from the balloon 30.

The insertion portion 12 is constituted by a flexible part 32, a curved part 34 and a leading end part 36. The curved part 34, which is constructed by connecting multiple nodal rings in a bendable manner, is bent in a remote control manner by the turning operation of the pair of angle knobs 22 provided in the manipulation portion 14. Accordingly, a leading end surface 37 of the leading end part 36 can be directed toward a predetermined direction.

Figure 2:
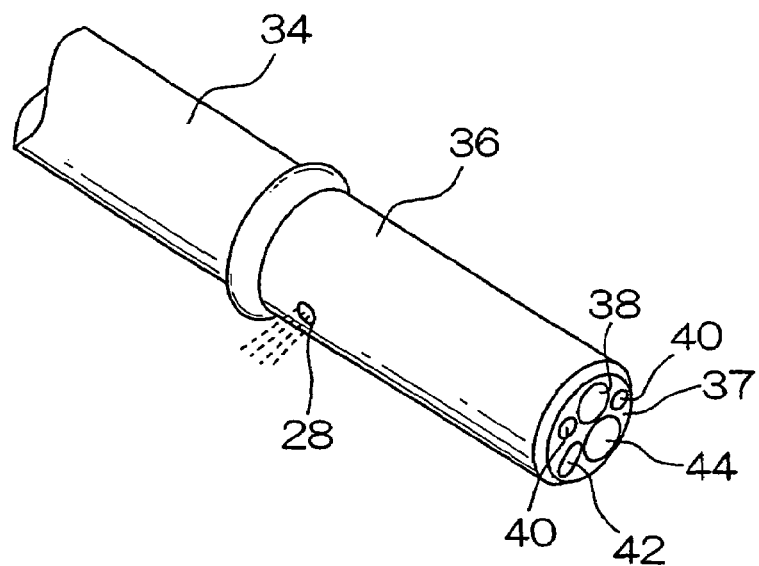
FIG. 2 is a perspective view of a leading end part of the insertion portion of the endoscope.
Figure 3:
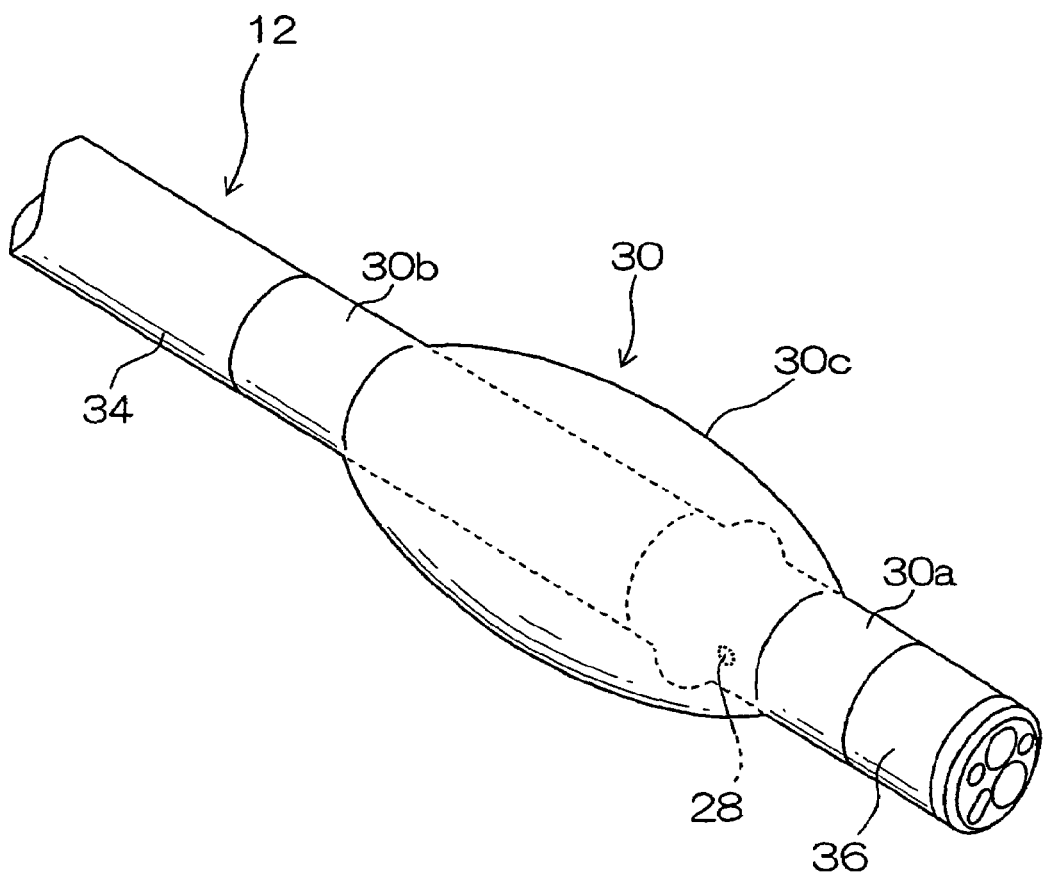
FIG. 3 is a perspective view of a leading end part of the insertion portion to which a first balloon is attached.

As shown in FIG. 2, an objective optical system 38, a lighting lens 40, an air feed and water feed nozzle 42, a forceps port 44, etc. are provided on the leading end surface 37 of th4e leading end part 36 in their respective positions. Furthermore, an air supply suction port 28 is provided on an outer peripheral surface of the leading end part 36 as shown in FIGS. 2 and 3, and this air supply suction port 28 is brought into communication with the balloon air feed port 26 of FIG. 1 via an air supply tube having an inside diameter of about 0.8 mm that is inserted into the interior of the insertion portion 12. Therefore, air is blown out of the air supply suction port 28 of the leading end part 36 by feeding air to the balloon air feed port 26, whereas air is sucked from the air supply suction port 28 by sucking air from the balloon air feed port 26.

As shown in FIG. 1, the first balloon 30 formed from an elastic body such as rubber is detachably mounted in the leading end part 36 of the insertion portion 12. As shown in FIG. 3, the first balloon 30 is constituted by a swollen part 30c in the middle and mounting parts 30a, 30b on both ends thereof, and the first balloon 30 is mounted on the leading end part 36 side in such a manner that the air supply suction port 28 is positioned inside the swollen part 30c. The mounting parts 30a, 30b, which are formed to provide a smaller diameter than the diameter of the leading end part 36, are fixed by winding a thread (not shown) after being brought into close contact with the leading end part 36 with elasticity. Incidentally, the fixing of the mounting parts 30a, 30b is not limited to this fixing by winding a thread, and the mounting parts 30a, 30b may be fixed to the leading end part 36 by fitting fixing rings over the mounting parts 30a, 30b.

In the first balloon 30 mounted on the leading end part 36, the swollen part 30c is dilated in roughly spherical shape by blowing out air from the air supply suction part 28 shown in FIG. 2. On the other hand, by sucking air from the air supply suction port 28, the swollen part 30c is deflated and brought into close contact with the outer peripheral surface of the leading end part 36.

Figure 4:
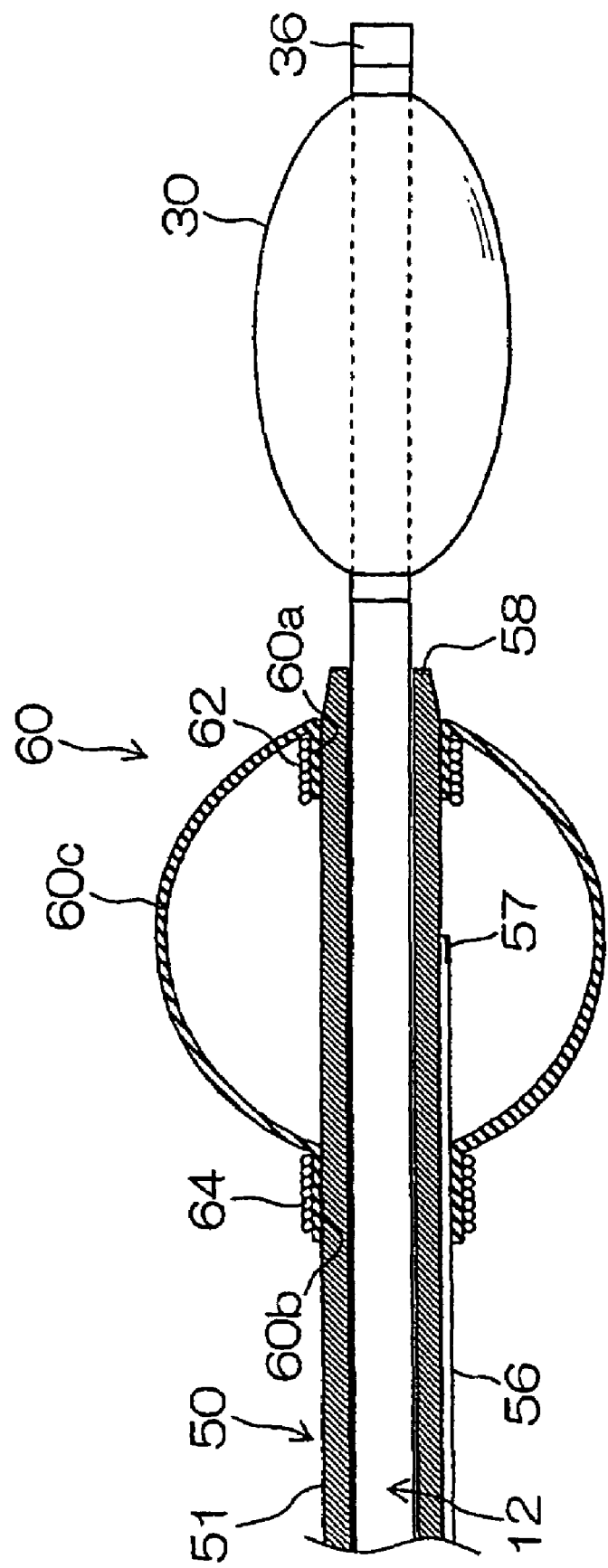
FIG. 4 is a side sectional view of an overtube.

The overtube 50 shown in FIG. 1 is constituted by a tube main body 51 and a grip 52. As shown in FIG. 4, the tube main body 51 is formed in cylindrical shape and has an inside diameter a little larger than the outside diameter of the insertion portion 12. In the tube main body 51, the outside of a flexible resin tube made of urethane or the like is coated with a lubricating coat and the inside is coated with a lubricating coat. Incidentally, as shown in FIGS. 1 and 4, the insertion portion 12 is inserted from a base end opening 52A of the grip 52 toward the tube main body 51.

As shown in FIG. 1, a balloon air feed port 54 is provided on the base end side of the tube main body 51. An air supply tube 56 having an inside diameter of about 1 mm is connected to the balloon air feed port 54, and the air supply tube 56 is bonded to the outer peripheral surface of the tube main body 51 and extended to the leading end part of the tube main body 51.

A leading end 58 of the tube main body 51 is formed in tapered shape. A second balloon 60 formed from an elastic body such as rubber is mounted on the base end side of the leading end 58 of the tube main body 51. The second balloon 60 is mounted, with the tube main body 51 piercing therethrough, and as shown in FIG. 4, this second balloon 60 is constituted by a swollen part 60c in the middle and mounting parts 60a, 60b on the both ends thereof. The mounting part 60a on the leading end side is folded back into the interior of the swollen part 60c, and the folded back mounting part 60a is fixed to the tube main body 51 by winding an X-ray contrast medium thread 62. The mounting part 60b on the base end side is arranged outside the second balloon 60 and fixed to the tube main body 51 by winding a thread 64.

The swollen part 60c is formed in roughly spherical shape in a natural condition (a condition that is neither inflated nor deflated) and the size of the swollen part 60c is larger than the size of the first balloon 30 in a natural condition (a condition that is neither inflated nor deflated). Therefore, when air is fed to the first balloon 30 and the second balloon 60 at the same pressure, the outside diameter of the swollen part 60c of the second balloon 60 becomes larger than the outside diameter of the swollen part 30c of the first balloon 30. The second balloon 60 is constructed in such a manner that the outside diameter of the second balloon 60 becomes φ50 mm when the outside diameter of the first balloon 30 is, for example, φ25 mm.

The above-described tube 56 is opened in the interior of the swollen part 60c and an air supply suction port 57 is formed. Therefore, when air is fed from the balloon feed air port 54, air is blown out of the air supply suction port 57 and the swollen part 60c is inflated. When air is sucked from the balloon feed air port 54, air is sucked from the air supply suction port 57 and the second balloon 60 is deflated. Incidentally, the reference numeral 66 of FIG. 1 deginates an injection port used to inject a lubricating liquid such as water into the tube main body 51, and this injection port 66 is brought into communication with the base end side of the tube main body 51 via a small-diameter tube 68. A lubricating liquid supply device 67 such as a pump or a syringe is connected to the injection port 66.

On the other hand, the balloon controller 100 of FIG. 1 is a device that performs the supply and suction of a fluid such as air to the first balloon 30 and also the supply and suction of a fluid such as air to the second balloon 60. The balloon controller 100 is constituted by a controller main body 102, which is provided with a pump, a sequencer, etc. (not shown), and a hand switch 104 for remote control.

A power switch SW1, a stop switch SW2, a pressure gauge 106 for the first balloon 30, and a pressure gauge 108 for the second balloon 60 are provided on a front panel of the controller main body 102. Also, a tube 110 that performs air supply and suction to the first balloon 30 and a tube 120 that performs air supply and suction to the second balloon 60 are also provided on the front panel of the controller main body 102. The tubes 110, 120 are midway provided with liquid storage tanks 130, 140 respectively that store body fluids which have flown back from the first balloon 30 and the second balloon 60 when the first balloon 30 and the second balloon 60 are broken.

On the other hand, the hand switch 104 is provided with a stop switch SW3 similar to the stop switch SW2 on the controller main body 102, an on/off switch SW4 that supports the pressurization/pressure reduction of the first balloon 30, a pause switch SW5 that holds the pressure of the first balloon 30, an on/off switch SW6 that supports the pressurization/pressure reduction of the second balloon 60, and a pause switch SW7 that holds the pressure of the second balloon 60. This hand switch 104 is electrically connected to the controller main body 102 via a cable 150.

The balloon controller 100 thus constructed inflates the first balloon 30 and the second balloon 60 by supplying air thereto and holds the first balloon 30 and the second balloon 60 in an inflated condition by controlling the air pressure. Also, the balloon controller 100 deflates the first balloon 30 and the second balloon 60 by sucking air therefrom and holds the first balloon 30 and the second balloon 60 in a deflated condition by controlling the air pressure.

The controller main body 102 is provided with a pressure sensor that indirectly detects the pressure of the first balloon 30 and the second balloon 60. This pressure sensor detects a pressuring force (for example, a pressure which is 5.6 kilopascal (kPa) higher than the atmospheric pressure) to appropriately fix the first balloon 30 and the second balloon 60 to the intestinal wall, an abnormal pressure higher than this pressuring force and a preset negative pressure. The controller main body 102 controls the above-described pumps on the basis of the pressure of the first balloon 30 and second balloon 60 detected by this pressure sensor.

Figure 5:
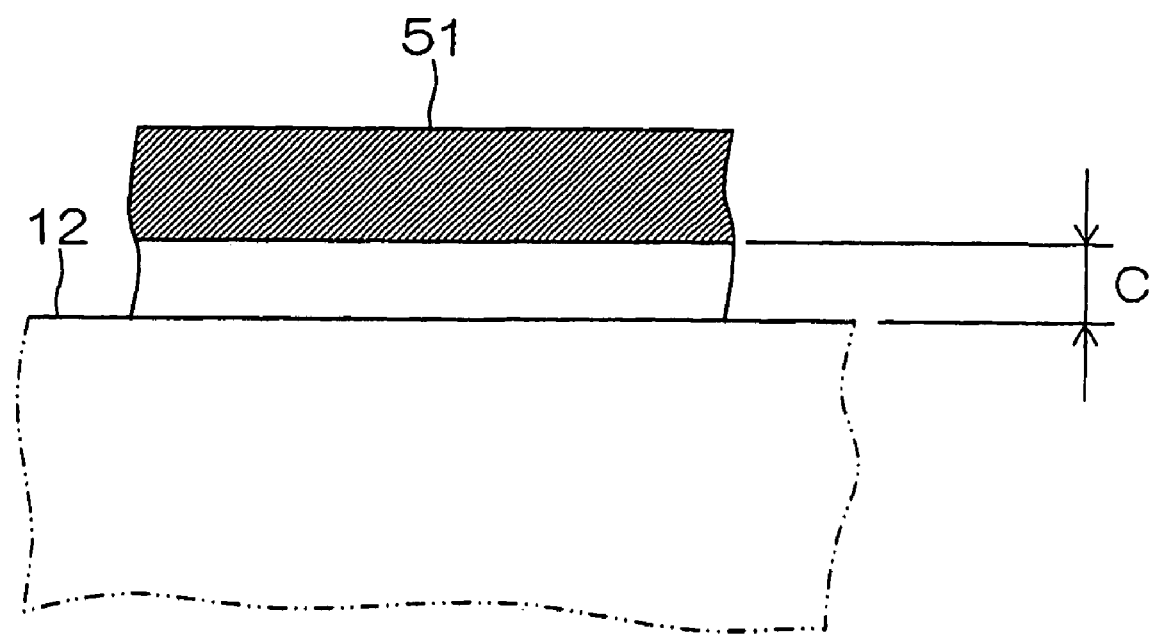
FIG. 5 is a partially enlarged sectional view of a gap between the overtube and the insertion portion of the endoscope.

Incidentally, in the endoscope apparatus of the embodiment, as shown in FIG. 5, the one-side gap C between the tube main body 51 of the overtube 50 and insertion portion 12 is set at 0.5 mm to 1.5 mm. By setting the one-side gap C at not less than 0.5 mm, a lubricating liquid such as water supplied from the injection port 66 (see FIG. 1) to the base end side of the tube main body 51 is sufficiently supplied to the whole area of the gap between the tube main body 61 and the insertion portion 12 and hence lubricity is improved. In a reverse case where the one-side gap C is less than 0.5 mm, a lubricating liquid is not sufficiently supplied to the whole area of the gap between the tube main body 61 and the insertion portion 12 and hence lubricity cannot be improved. Also, by setting the one-side gap C at not more than 1.5 mm, the snaking of the insertion portion 12 with respect to the tube main body 51 can be held to a minimum. As a result of this, the insertion and extraction operability of the insertion portion 12 with respect to the overtube 50 is improved. Incidentally, the one-side gap C is half a maximum gap when the insertion portion 12 is caused to abut against the inner circumferential surface of the tube main body 51.

Next, how to operate the endoscope apparatus will be described on the basis of FIG. 6A to FIG. 6H.

First, as shown in FIG. 6A, the insertion portion 12 is inserted into the intestinal tract (for example, the descending limb of the duodenum) 70, with the overtube 50 covering the insertion portion 12. At this time, the first balloon 30 and the second balloon 60 are deflated beforehand.

Next, as shown in FIG. 6B, the second balloon 60 is inflated by supplying air thereto, with the leading end 58 of the overtube 50 inserted up to a curvature of the intestinal tract 70. As a result of this, the second balloon 60 is locked to the intestinal tract 70 and the leading end 58 of the overtube 50 is fixed to the intestinal tract 70.

Next, as shown in FIG. 6C, only the insertion portion 12 of the endoscope 10 is inserted into a deep part of the intestinal tract 70. And as shown in FIG. 6D, the first balloon 30 is inflated by supplying air thereto. As a result of this, the first balloon 30 is fixed to the intestinal tract 70. On that occasion, the size of the first balloon 30 in an inflated condition is smaller than the size of the second balloon 60 and, therefore, a load on the intestinal tract 70 is small, with the result that damage to the intestinal tract 70 can be prevented.

Subsequently, after the second balloon 60 is deflated by sucking air from the second balloon 60, as shown in FIG. 6E, the overtube 50 is pushed in and inserted along the insertion portion 12. And after the leading end 58 of the overtube 50 is pushed in to near the first balloon 30, as shown in FIG. 6F, the second balloon 60 is inflated by supplying air thereto. As a result of this, the second balloon 60 is fixed to the intestinal tract 70. That is, the intestinal tract 70 is gripped by the second balloon 60.

Next, as shown in FIG. 6G, the overtube 50 is pulled toward the surgical operator. As a result of this, the intestinal tract 70 becomes contracted substantially straight and extra deflections and curvatures of the overtube 50 varnish. Incidentally, when the overtube 50 is pulled toward the surgical operator, both the first balloon 30 and the second balloon 60 are locked to the intestinal tract 70. However, the frictional resistance of the first balloon 30 is smaller than the frictional resistance of the second balloon 60. Therefore, even when the first balloon 30 and the second balloon 60 move away relatively, the intestinal tract 70 will not be damaged by being stretched by the two balloons 30, 60, because the first balloon 30 of small frictional resistance slides with respect to the intestinal tract 70.

Subsequently, as shown in FIG. 6H, the first balloon 30 is deflated by sucking air therefrom. And the leading end part 36 of the insertion portion 12 is inserted into a deep part of the intestinal tract 70 as far as possible. That is, the insertion operation shown in FIG. 6C is performed again. As a result of this, it is possible to insert the leading end part 36 of the insertion portion 12 into a deep part of the intestinal tract 70. When the insertion portion 12 is to be inserted into a deeper part, the pushing-in operation shown in FIG. 6E is performed after the fixing operation shown in FIG. 6D is performed, and moreover the gripping operation shown in FIG. 6F, the operation of pulling toward the surgical operator shown in FIG. 6G and the insertion operation shown in FIG. 6H are repeated in this order. As a result of this, the insertion portion 12 can be inserted into a deeper part of the intestinal tract 70.

In such a surgical operation, because in the endoscope apparatus of the embodiment the one-side gap C between the tube main body 51 of the overtube 50 and the insertion portion 12 is set at 0.5 mm to 1.5 mm, a lubricating liquid can be sufficiently supplied to the whole area of the gap between the tube main body 61 and the insertion portion 12 and lubricity is improved. Also, because the one-side gap C is set at not more than 1.5 mm, the snaking of the insertion portion 12 with respect to the tube main body 51 can be held to a minimum and the insertion and extraction operability of the insertion portion 12 with respect to the overtube 50 is improved.

On the other hand, in a treatment performed with the aid of an endoscope apparatus in which the overtube 50 is used, there is a case where after the insertion of the overtube 50 and the insertion portion 12 of the endoscope into an aimed part within a body cavity, operative instruments, such as a balloon dilator that dilates the narrow areas of the intestinal tract and a contrast medium tube that injects a contrast medium for observing narrow areas of the intestinal tract are inserted to perform a desired treatment.

In this case, it is conceivable that only the insertion portion 12 of the endoscope is extracted, with the overtube 50 kept remaining in the body cavity, and these operative instruments are inserted by using the overtube 50 as a guide. Accordingly, it becomes necessary that in an endoscope apparatus of the balloon type, the first balloon 30 which has been deflated be removed via the gap C between the overtube 50 and the insertion portion 12 of the endoscope. However, the thickness of the first balloon 30 made of natural rubber is as small as about 0.1 mm and the thickness of creases formed by the deflation of the first balloon 30 is also about 0.3 mm. Therefore, because the first balloon 30 can be extracted from the overtube 50 without a resistance in the endoscope apparatus of the present invention in which the one-side gap is set at not less than 0.5 mm, the insertion portion of the endoscope can be extracted from the overtube 50 without problems.

Incidentally, the overtube 50 is exemplified as an insertion aid in the embodiment. However, an insertion aid is not limited to this and a sliding tube that is inserted per anus may be used.

FIG. 7 is a system configuration diagram of an endoscope apparatus in which the supply of a lubricating liquid to the overtube 50 is automated. Members that are the same with or similar to the endoscope apparatus shown in FIG. 1 are given the same reference numerals as in FIG. 1 and descriptions of these members are omitted.

The endoscope apparatus shown in the figure is provided with a strain gauge (sensor) 200 used to measure frictional resistance values (load resistance values) between the insertion portion 12 of the endoscope and the overtube 50 and a control section 204 that controls the opening and closing of a solenoid valve for lubricating liquid supply (a lubricating liquid supply device) 202 on the basis of signals outputted from the strain gauge 200.

The strain gauge 200, which is stuck to the insertion portion 12 of the endoscope, detects strains of the insertion portion 12 of the endoscope generated by the relative insertion and extraction motions of the insertion portion 12 and the overtube 50. Incidentally, the strain gauge 200 may be installed on the overtube 50 side.

An electrical signal that indicates strains from the strain gauge 200 are outputted in the control section 204, and the control section 204 calculates a frictional resistance value corresponding to the electrical signal. This frictional resistance value is a load resistance value between the insertion portion 12 of the endoscope and the overtube 50. And when this value exceeds a prescribed frictional resistance value (threshold value) that has been set beforehand, the control section 204 performs the control of the solenoid valve 202 so as to open the solenoid valve 202. As a result of this, a lubricating liquid 208 stored in a tank 206 is supplied by gravity from the injection port 66 to the base end side of the tube main body 51. And when a calculated frictional resistance value becomes lower than the above-described prescribed frictional resistance value (threshold value) that has been set beforehand, the control section 204 performs the control of the solenoid valve 202 so as to close the solenoid valve 202.

Because the lubricating liquid 208 is used to lessen load resistance between the insertion portion 12 of the endoscope and the overtube 50, it is unnecessary to constantly supply the lubricating liquid 208 from the tank 206. For this reason, frictional resistance between the insertion portion 12 of the endoscope and the overtube 50 is measured with the strain gauge 200 and the control section 204, and the control section 204 performs the supply of the lubricating liquid 208 by performing the control of the solenoid valve 202 so as to open the solenoid valve 202 when a measured frictional resistance value exceeds a prescribed value.

As a result of this, the lubricating liquid 208 can be saved because useless supply of the lubricating liquid 208 can be prevented. Also, because relative insertion and extraction resistance of the insertion portion 12 of the endoscope and the overtube 50 becomes almost constant, stable operative treatment becomes possible. Furthermore, if an automatic insertion device of the insertion portion of the endoscope and of the overtube is used in combination, this is favorable for automation.

Incidentally, as the automatic supply of a lubricating liquid, details of the control of the opening and closing of the solenoid valve 202 by the control section 204 were described above. However, in the case of an endoscope apparatus in which the lubricating liquid 208 is fed to the injection port 66 by use of a pump, it is necessary only that the control section 204 control the drive on/off of the pump.

What is claimed is:

1. An endoscope apparatus, comprising:

an endoscope;

an insertion aid through which an insertion portion of the endoscope is movably inserted and extracted;

a lubricating liquid supply device that supplies a lubricating liquid to a gap between the insertion aid and the insertion portion of the endoscope; and a strain sensor attached to one of the insertion portion of the endoscope and the insertion aid, said sensor detecting a strain of the insertion portion of the endoscope or the insertion aid generated by the relative insertion and extraction motions of the insertion portion of the endoscope and the insertion aid, wherein the lubricating liquid supply device supplies a lubricating liquid on the basis of the strain detected by the strain sensor, and wherein the gap between the insertion aid and the insertion portion of the endoscope is set at 0.5 mm to 1.5 mm.

2. The endoscope apparatus according to claim 1, further comprising a balloon attached to an outer peripheral part of a leading end of the insertion portion of the endoscope and/or an outer peripheral part of a leading end of the insertion aid.

* * * * *